United States Patent
Shie

(10) Patent No.: US 11,382,838 B2
(45) Date of Patent: Jul. 12, 2022

(54) NASOGASTRIC TUBE STRUCTURE

(71) Applicant: Chang-Bih Shie, Tainan (TW)

(72) Inventor: Chang-Bih Shie, Tainan (TW)

( * ) Notice: Subject to any disclaimer, the term of this patent is extended or adjusted under 35 U.S.C. 154(b) by 0 days.

(21) Appl. No.: 16/433,130

(22) Filed: Jun. 6, 2019

(65) Prior Publication Data

US 2020/0289377 A1 Sep. 17, 2020

(30) Foreign Application Priority Data

Mar. 15, 2019 (TW) .................................. 108108941

(51) Int. Cl.
*A61J 15/00* (2006.01)
*A61B 90/00* (2016.01)

(52) U.S. Cl.
CPC ......... *A61J 15/0003* (2013.01); *A61J 15/003* (2013.01); *A61J 15/0073* (2013.01); *A61B 90/361* (2016.02)

(58) Field of Classification Search
CPC ................ A61J 15/0003; A61J 15/0015; A61J 15/0023; A61J 15/0073; A61J 15/003; A61J 15/0057; A61J 15/0061; A61J 15/0034; A61M 16/04; A61M 16/0434; A61M 39/288; A61M 39/28; A61M 2025/024; A61M 16/0666; A61M 16/0461; A61M 2039/0255; A61M 2025/0681

See application file for complete search history.

(56) References Cited

U.S. PATENT DOCUMENTS

| | | | | |
|---|---|---|---|---|
| 186,503 A * | 1/1877 | Snook | ..................... | F16B 7/048 |
| | | | | 403/190 |
| 2,653,787 A * | 9/1953 | Myrick | ............... | A61M 39/284 |
| | | | | 251/10 |
| 4,015,313 A * | 4/1977 | Oldford | .................. | F16L 25/04 |
| | | | | 24/277 |
| 6,135,111 A * | 10/2000 | Mongeon | .......... | A61M 16/0475 |
| | | | | 128/207.15 |
| 9,849,070 B2 * | 12/2017 | Elia | ........................ | A61B 1/015 |
| 2003/0225392 A1 * | 12/2003 | McMichael | ......... | A61J 15/0069 |
| | | | | 604/509 |
| 2009/0275825 A1 * | 11/2009 | Thomas | ............... | A61J 15/0088 |
| | | | | 600/424 |
| 2013/0338521 A1 * | 12/2013 | Thompson | ........ | A61M 16/0484 |
| | | | | 600/532 |
| 2016/0038014 A1 * | 2/2016 | Molnar | .............. | A61B 1/00137 |
| | | | | 600/109 |
| 2017/0189273 A1 * | 7/2017 | Hsu | ...................... | A61J 15/0003 |
| 2017/0296713 A1 * | 10/2017 | Lobo | ....................... | A61M 1/80 |

FOREIGN PATENT DOCUMENTS

WO   WO-2017114310 A1 *   7/2017   ............ A61J 15/008

* cited by examiner

*Primary Examiner* — James D Ponton
*Assistant Examiner* — Neeraja Gollamudi
(74) *Attorney, Agent, or Firm* — Rosenberg, Klein & Lee

(57) ABSTRACT

A nasogastric tube structure is disclosed which comprises a first tube, a clamping member and a positioning member. The first tube has a front necking opening, a rear opening, a stopper ring on a wall thereof adjacent to the rear opening and an engaging groove on the wall thereof adjacent to the stopper ring. The clamping member comprises two corresponding positioning segments and a C-shaped clip portion for connecting the two positioning segments and engaging with the engaging groove. The positioning member is sleeved on the two positioning segments.

13 Claims, 22 Drawing Sheets

NASOGASTRIC TUBE STRUCTURE

BACKGROUND OF THE INVENTION

1. Field of the Invention

The present invention relates to a nasogastric tube structure which is inserted into the stomach auxiliary by a transnasal gastroscope.

2. DESCRIPTION OF RELATED ART

For a person or an animal who is malnourished, insufficient in electrolyte or water caused by difficulties in chewing and swallowing, choking, coughing, spending too much time for eating and intaking too little foods, or for a person or an animal who is unconscious and cannot intake food by himself/herself/itself, a nasogastric tube is needed to deliver fluid nutrients directly to the stomach in which the nasogastric tube is inserted to the stomach of the person or the animal abovementioned by a doctor. Delivering fluid nutrients by a nasogastric tube reduces choking and coughing of a patient or an animal caused by eating, maintains the life of the patient or the animal, and saves time and manpower for a caregiver to feed the patient or the animal.

Although the nasogastric tube is a life-support device to feed the patient quickly, it has a risk to cause infection since inserting the nasogastric tube from the nasal cavity for passing through the esophagus to reach the stomach of one needed is an invasive medical behavior. In addition, when a nasogastric tube is applied to an unconscious patient or animal, the patient or the animal will not give a response to a medical staff when the nasogastric tube is inserted into the bronchi accidently which leads to aspiration pneumonia after feeding and affects the health of the patient or the animal seriously. Therefore, the probability of causing infection when inserting a nasogastric tube into the stomach of the patient needs to be reduced.

SUMMARY OF THE INVENTION

The present invention is developed by a gastroenterologist who hopes to dissolve disadvantages of using a conventional nasogastric tube in clinical.

The present invention relates to a nasogastric tube structure which is sleeved on a transnasal gastroscope and inserted into the stomach successfully with the help of a camera and a feature of controllable forward direction of the transnasal gastroscope.

The main purpose and effect of the present invention is achieved by the following technical means:

The nasogastric tube structure of the present invention comprises a first tube, a clamping member and a positioning member. The first tube has a front necking opening, a rear opening corresponding to the front necking opening, at least one through hole penetrating a wall thereof adjacent to the front necking opening, and an engaging groove adjacent to the rear opening. The clamping member comprises two corresponding positioning segments and a C-shaped clip portion connected to the two positioning segments by two ends thereof and engaged with the engaging groove of the first tube. The positioning member sleeves on the two positioning segments of the clamping member simultaneously hold the two positioning segments as closely as possible to generate a bundling and fixing force.

The advantages of the present invention are described as follows:

The nasogastric tube structure of the present invention is sleeved on a transnasal gastroscope and inserted into the stomach of a patient by a medical staff successfully with the help of a camera of the transnasal gastroscope which sends images back to the medical staff and has a feature of controllable forward direction. Therefore, the nasogastric tube structure of the present invention is convenient in use and decreases a risk of infection.

DETAILED DESCRIPTION OF THE PREFERRED EMBODIMENT

Figure 1:
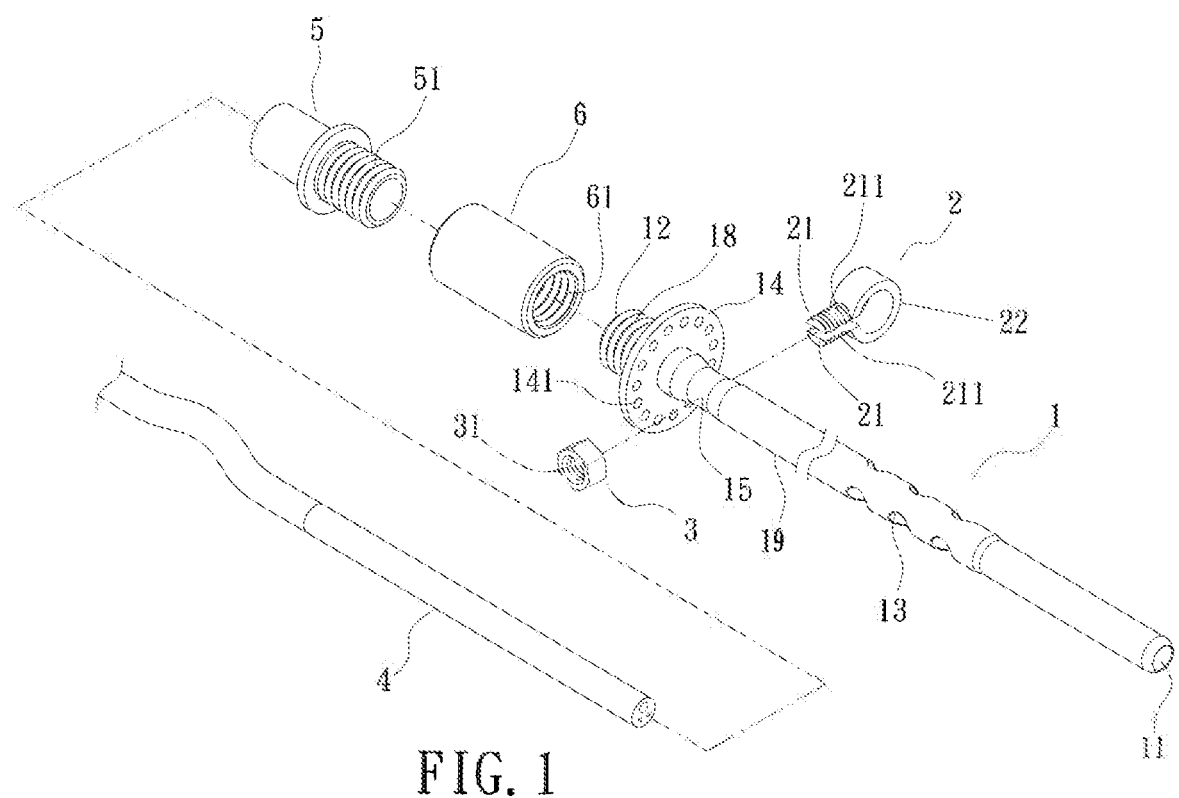
FIG. 1 is an exploded diagram showing a first embodiment for a nasogastric tube structure and a transnasal gastroscope of the present invention.

Referring to FIG. 1 to FIG. 4, the nasogastric tube structure of the present invention comprises a first tube (1), a clamping member (2) and a positioning member (3).

The first tube (1) has a front necking opening (11) at a first terminal thereof, a rear opening (12) at a second terminal thereof corresponding to the first terminal, an intermediate portion (19) extending between the front necking opening (11) and rear opening (12) (that is, between the first and second terminals), at least one through hole (13) penetrating a wall thereof adjacent to the front necking opening (11), a stopper ring (14) disposed on the wall thereof adjacent to the rear opening (12) and having plural apertures (141), and an engaging groove (15) on the wall thereof adjacent to the stopper ring (14) and the rear opening (12). In the embodiment illustrated in FIGS. 1-4, engaging groove (15) defines an annular recess on the intermediate portion (19). When the first tube (1) is sleeved on a transnasal gastroscope (4), a camera at a front end of the transnasal gastroscope (4) is exposed in the front necking opening (11) and not protruded from the front necking opening (11) because of the front necking opening (11) has a necking portion.

The clamping member (2) comprises two corresponding positioning segments (21) and a C-shaped clip portion (22) connected to the two positioning segments (21) by two ends thereof for correspondingly engaging with the engaging groove (15) of the first tube (1).

The positioning member (3) is sleeved on the two positioning segments (21) simultaneously for holding the two positioning segments (21) closely to generate a bundling and fixing force by the C-shaped clip portion (22). The bundling and fixing force of the C-shaped clip portion (22) positions and fixes the transnasal gastroscope (4) with the first tube (1) and prevents the transnasal gastroscope (4) sliding away from the first tube (1).

In one embodiment in FIG. 1 to FIG. 4, each of the two positioning segments (21) has an outer screw thread (211) at an outer surface, and the positioning member (3) has an inner screw thread (31) for screwing the outer screw thread (211) of each of the two positioning segments (21) to fix the position member (3).

Figure 5:
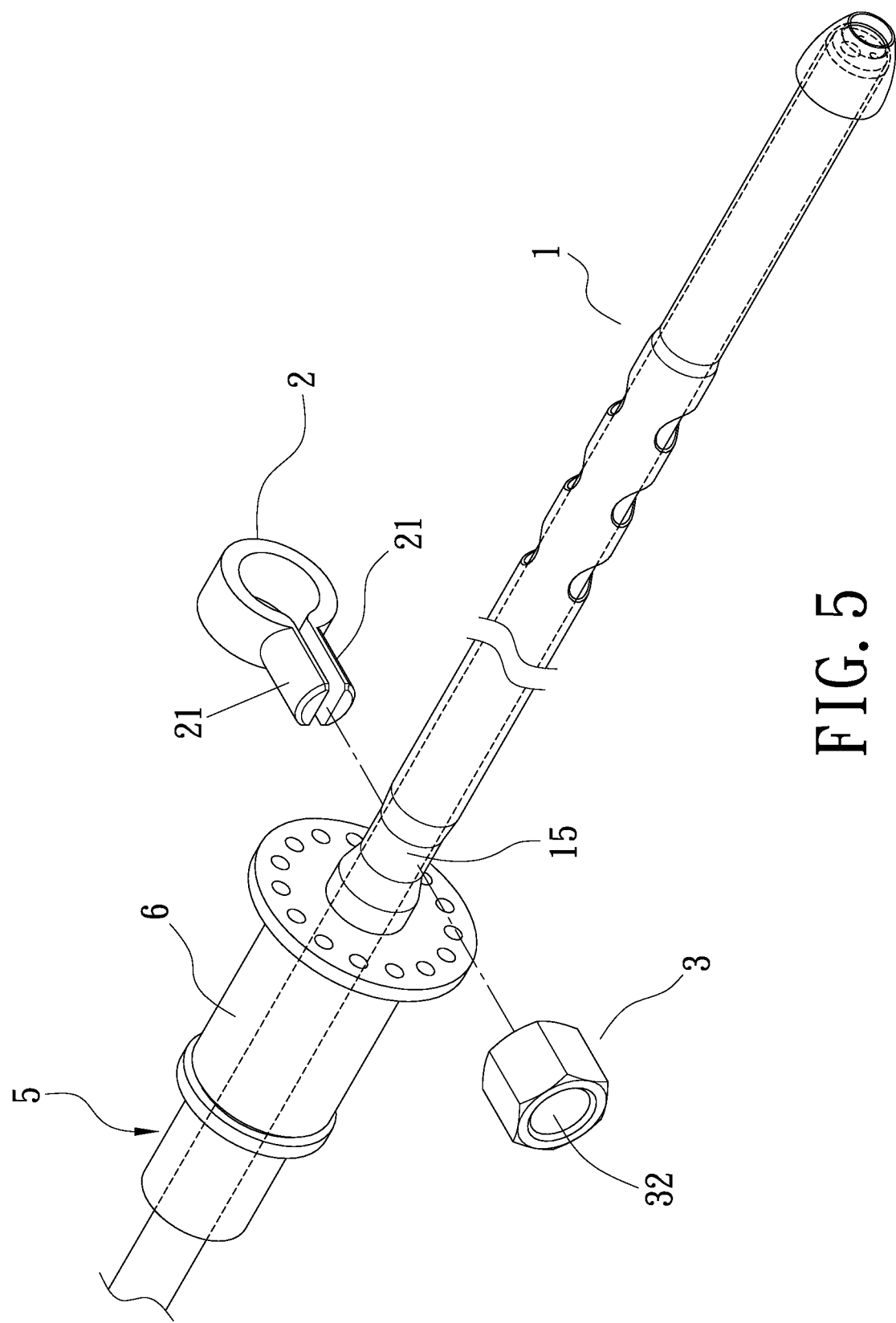
FIG. 5 is a schematic diagram showing a second embodiment for a positioning member of the present invention.
Figure 6:
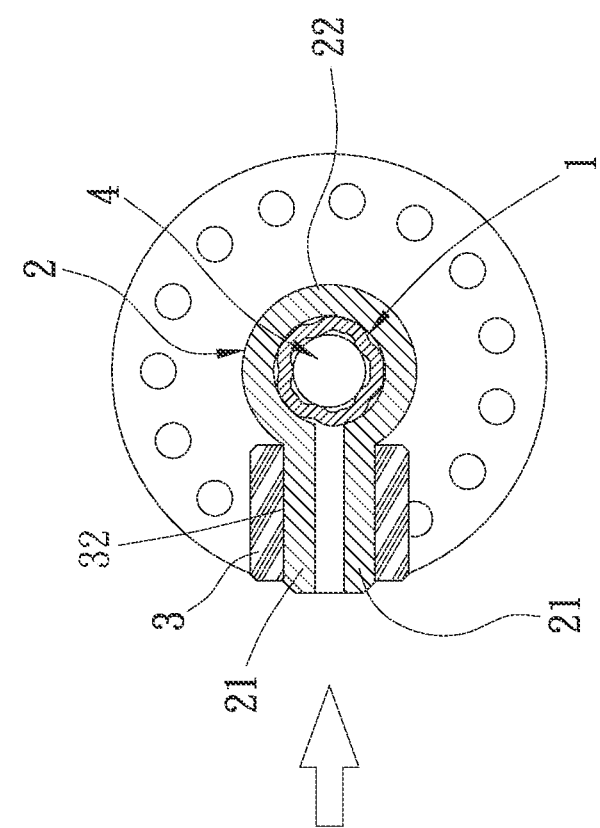
FIG. 6 is a front sectional view showing the positioning member unfixed and fixed with two positioning segments in the second embodiment of the present invention.
Figure 6:
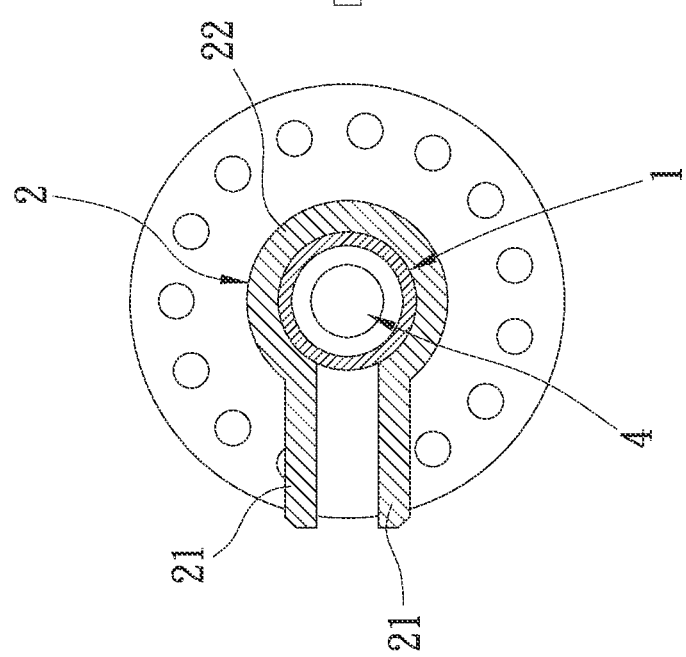

In one embodiment in FIG. 5 and FIG. 6, the positioning member (3) has a tunnel (32) for sleeving the two positioning segments (21) and fixing the positioning member (3) to the two positioning segments (21).

Referring to FIG. 1 to FIG. 4, to insert the nasogastric tube structure of the present invention into the stomach, the first tube (1) of the nasogastric tube structure is first sleeved on the transnasal gastroscope (4) and the camera of the transnasal gastroscope (4) is exposed in the front necking opening (11) at the first terminal of the first tube (1). The transnasal gastroscope (4) does not protrude from the front necking opening (11) because a diameter of the front necking opening (11) is less than a diameter of a front end of the transnasal gastroscope (4). Then, the C-shaped clip portion (22) of the clamping member (2) is engaged with the engaging groove (15) of the first tube (1), and the positioning member (3) is sleeved on the two positioning segments (21) of the clamping member (2) to bundle and fix the first tube (1) with the transnasal gastroscope (4) by a bundling and fixing effect of the clamping member (2) and the positioning member (3). The camera of the transnasal gastroscope (4) sends back images of the location of the nasogastric tube structure to a medical staff member who is inserting the nasogastric tube structure into the stomach of a patient, and the medical staff can control a forward direction of the nasogastric tube structure for inserting the nasogastric tube structure into the stomach successfully.

After the nasogastric tube structure is inserted into the stomach, the positioning member (3) is taken off from the positioning segments (21) of the clamping member (2) for removing the transnasal gastroscope (4) from the nasogastric tube structure and leaving the nasogastric tube structure inside the body for tube feeding.

Figure 7:
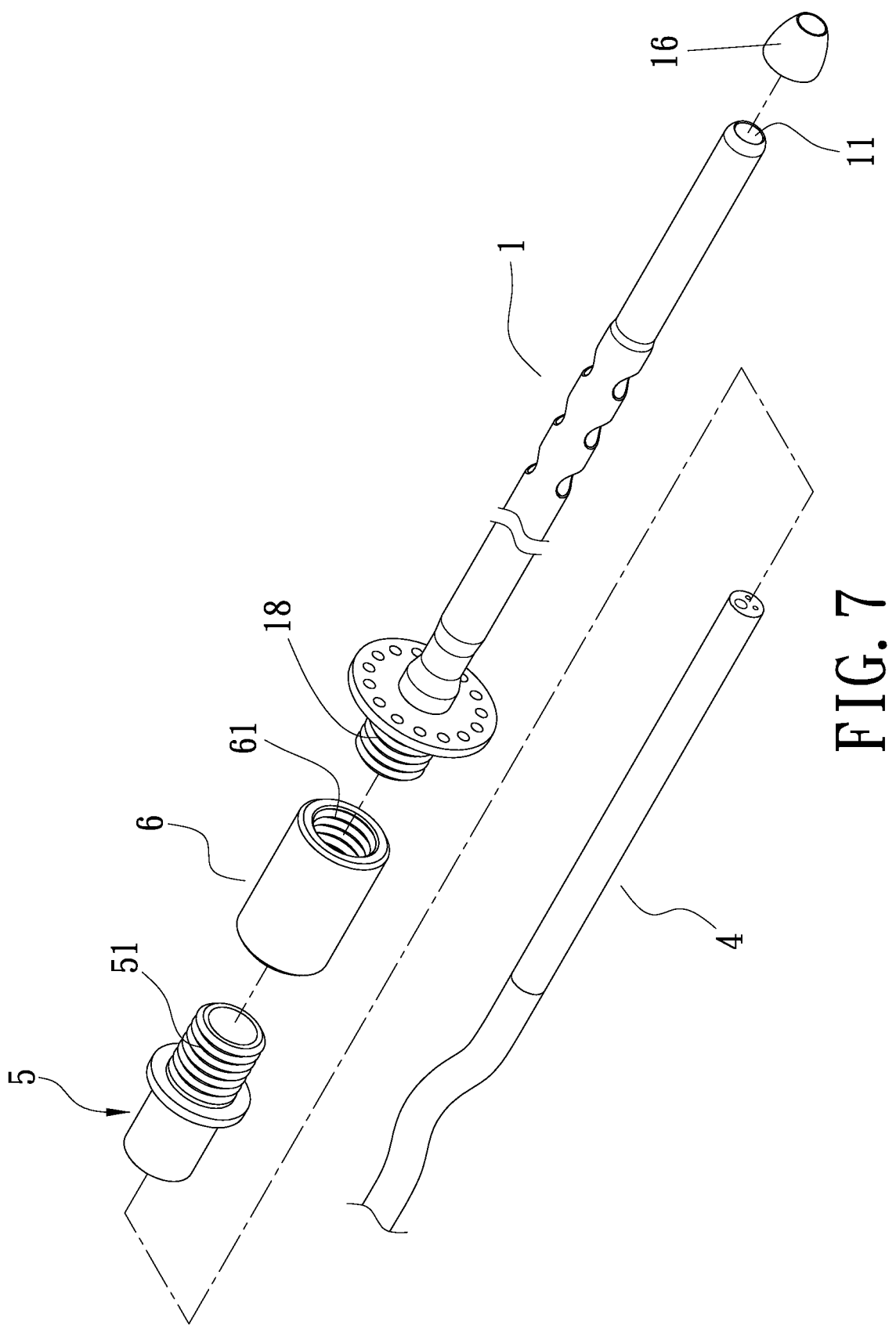
FIG. 7 is an exploded diagram showing a cap placed at a front necking opening of a first tube of the present invention.
Figure 8:
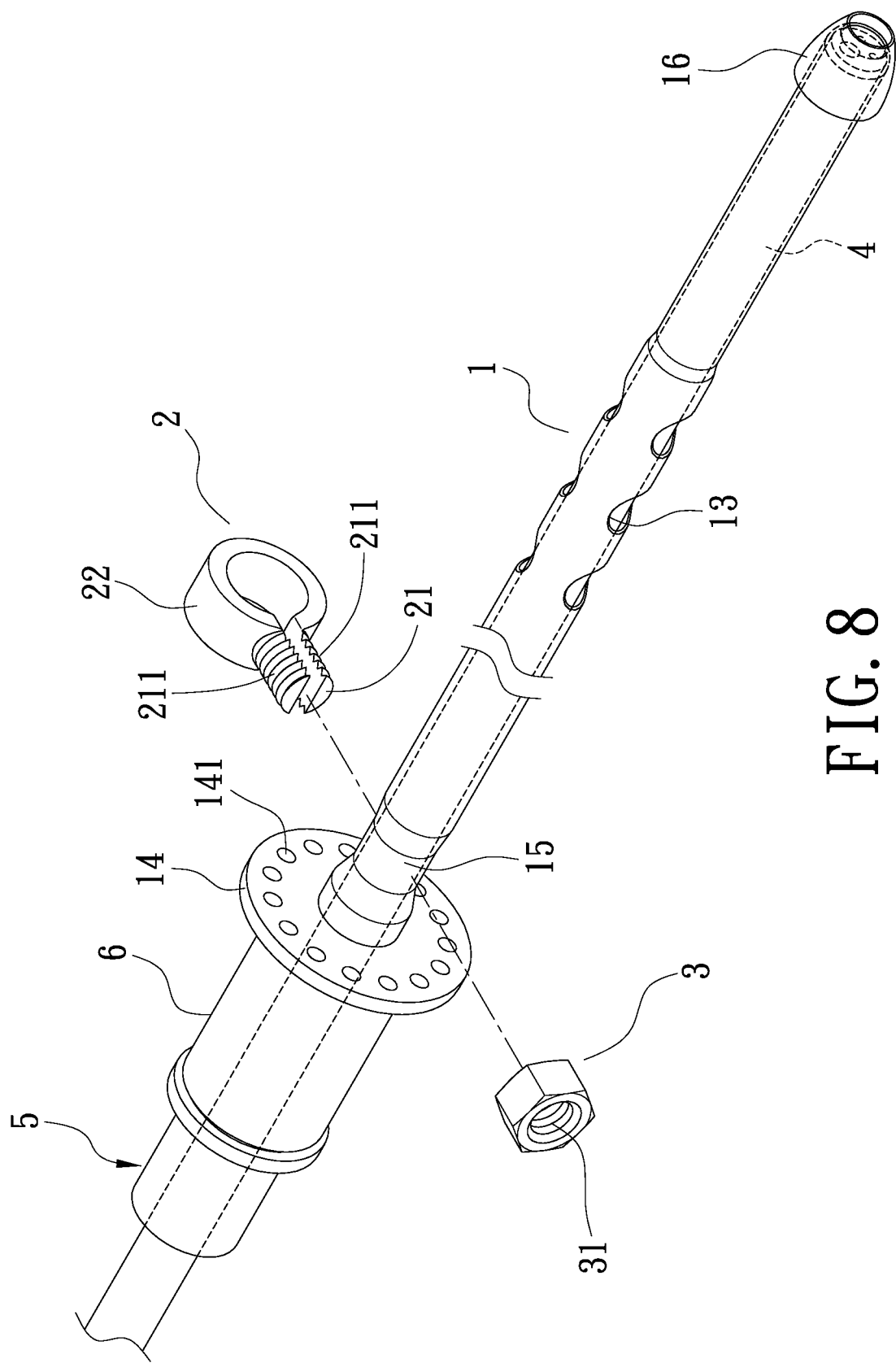
FIG. 8 is a stereogram showing a nasogastric tube structure sleeved on a transnasal gastroscope according to FIG. 7 of the present invention in which a positioning member is unfixed with two positioning segments.
Figure 9:
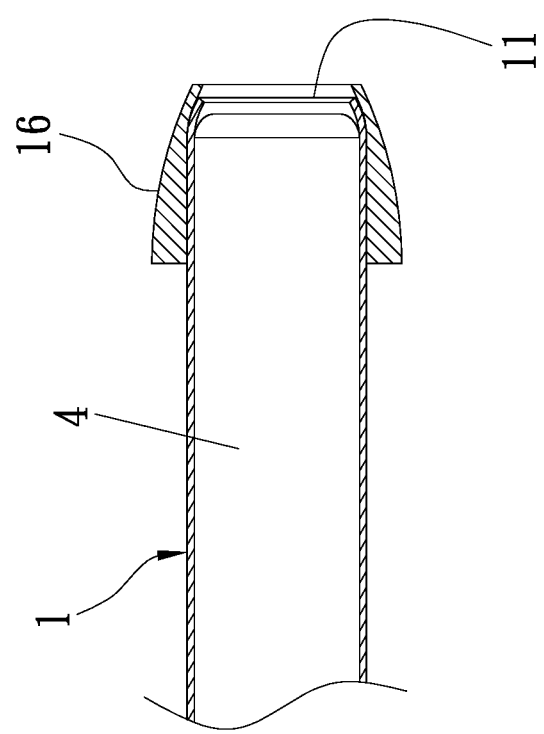
FIG. 9 is a partial enlarged sectional view showing a first type of cap placed at a front necking opening of a first tube of the present invention.

Referring to FIG. 7 to FIG. 9, in one embodiment of the present invention, a conical cap (16) is further sleeved on the front necking opening (11) of the first tube (1). The cap (16) is coated with a metal photosensitive layer on a surface thereof and the exact location of the cap (16) can be detected by a X-ray machine. In addition, the cap (16) also prevents the transnasal gastroscope (4) protruding from the front necking opening (11).

Figure 10:
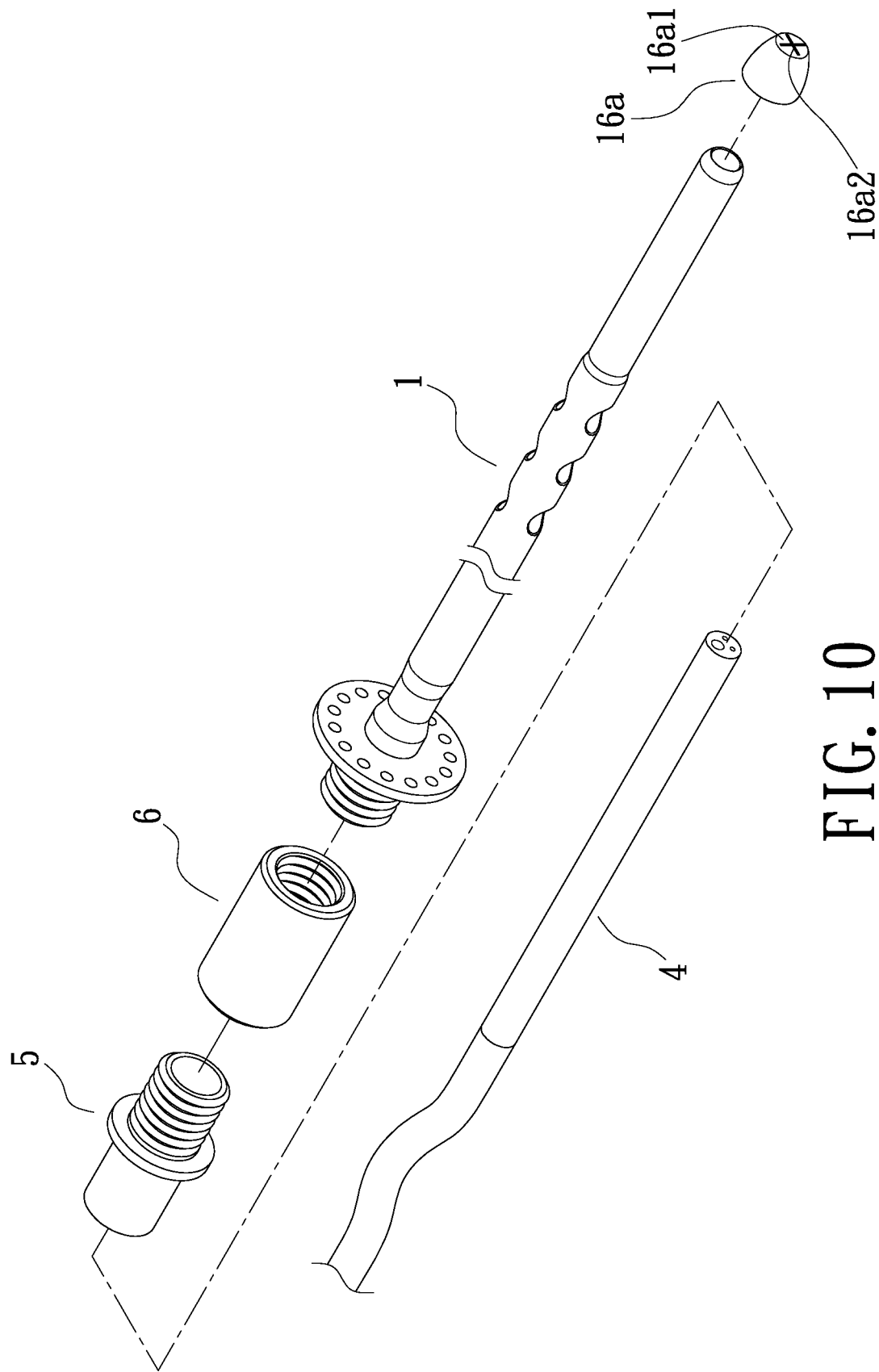
FIG. 10 is an exploded diagram showing a second type of cap placed at a front necking opening of a first tube of the present invention.
Figure 11:
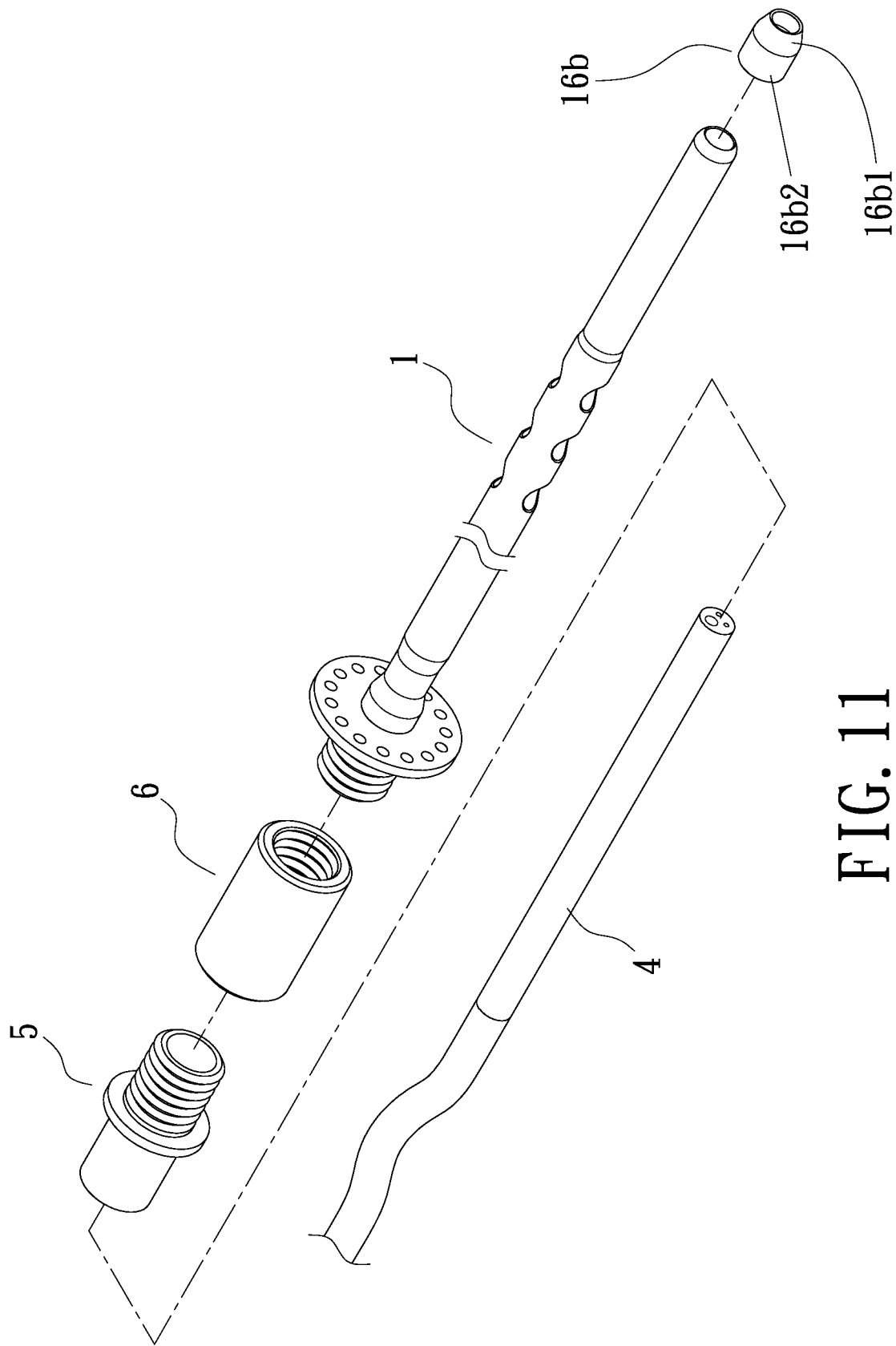
FIG. 11 is an exploded diagram showing a third type of cap placed at a front necking opening of a first tube of the present invention.
Figure 12:
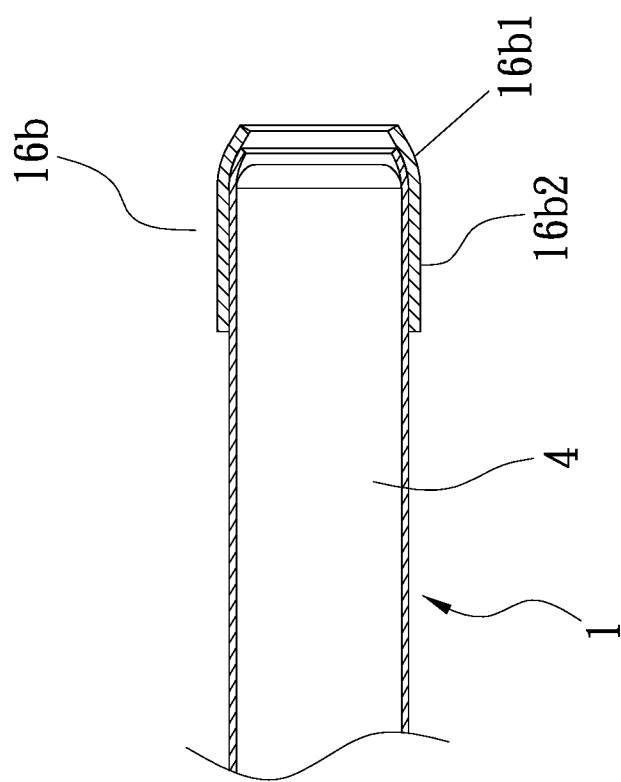
FIG. 12 is a partial enlargement sectional view showing a third type of cap placed at a front necking opening of a first tube of the present invention.
Figure 13:
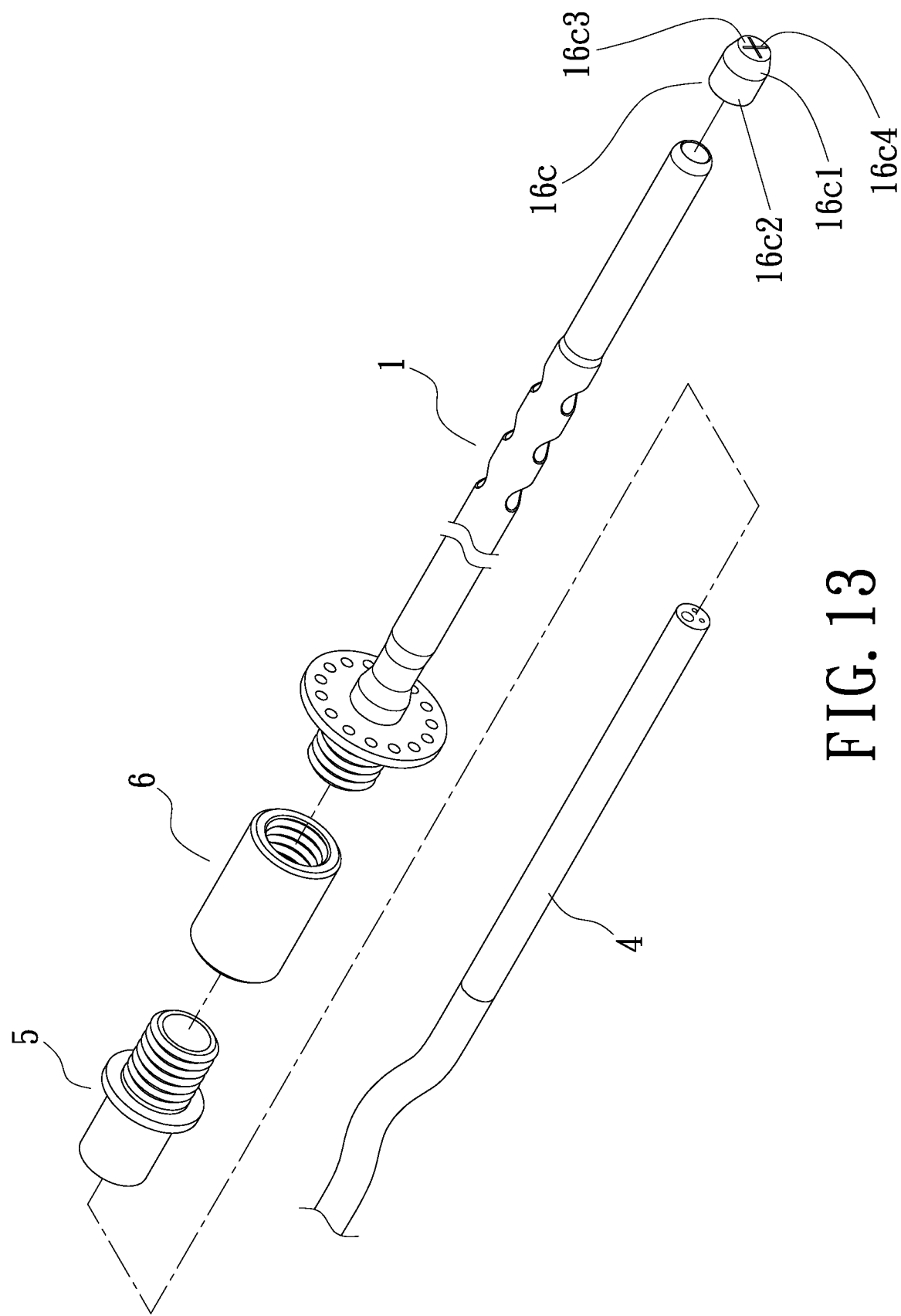
FIG. 13 is an exploded diagram showing a fourth type of cap placed at a front necking opening of a first tube of the present invention.

Referring to FIG. 10 to FIG. 13, three types of the caps (16) are disclosed. In FIG. 10, the cap (16a) has a top surface (16a1) at a front end thereof and a cross cut (16a2) on the top surface (16a1). The cap (16a) also prevents the transnasal gastroscope (4) protruding from the front necking opening (11). In FIG. 11 and FIG. 12, the cap (16b) has a conical section (16b1) at a front end thereof and a ring section (16b2) connected to a back end of the conical section (16b1). The diameter of the conical section (16b1) is also less than the diameter of the transnasal gastroscope (4), so the transnasal gastroscope (4) cannot protrude from the front necking opening (11). In FIG. 13, the cap (16c) has a conical section (16c1) at a front region thereof and a ring section (16c2) connected to a back end of the second conical section (16c1). The cap (16c) in FIG. 13 further has a top surface (16c3) at a front end thereof and a cross cut (16c4) on the top surface (16c3).

Figure 2:
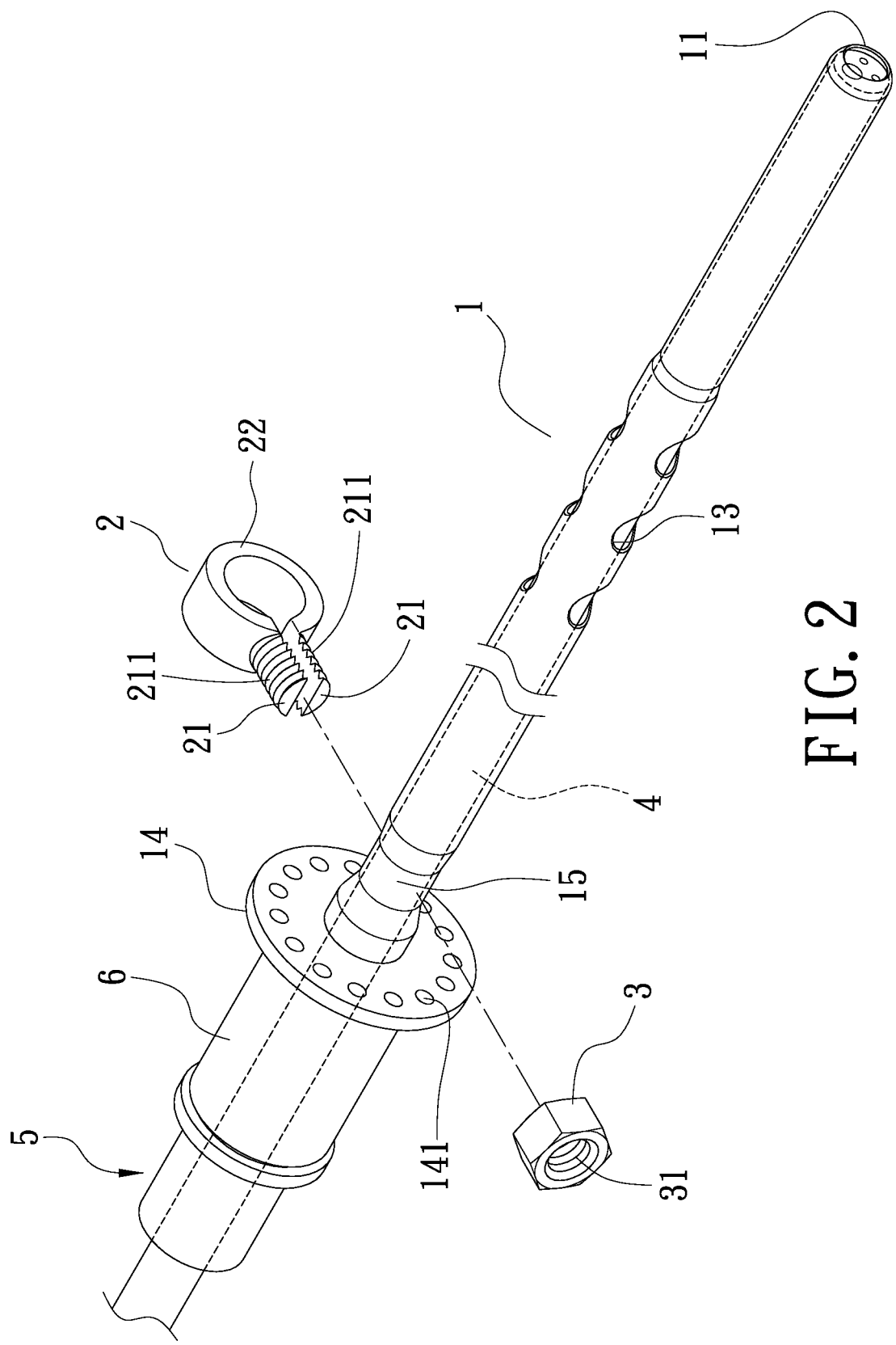
FIG. 2 is a stereogram showing the nasogastric tube structure sleeved on the transnasal gastroscope in the first embodiment of the present invention in which a positioning member is not fixed with two positioning segments.
Figure 3:
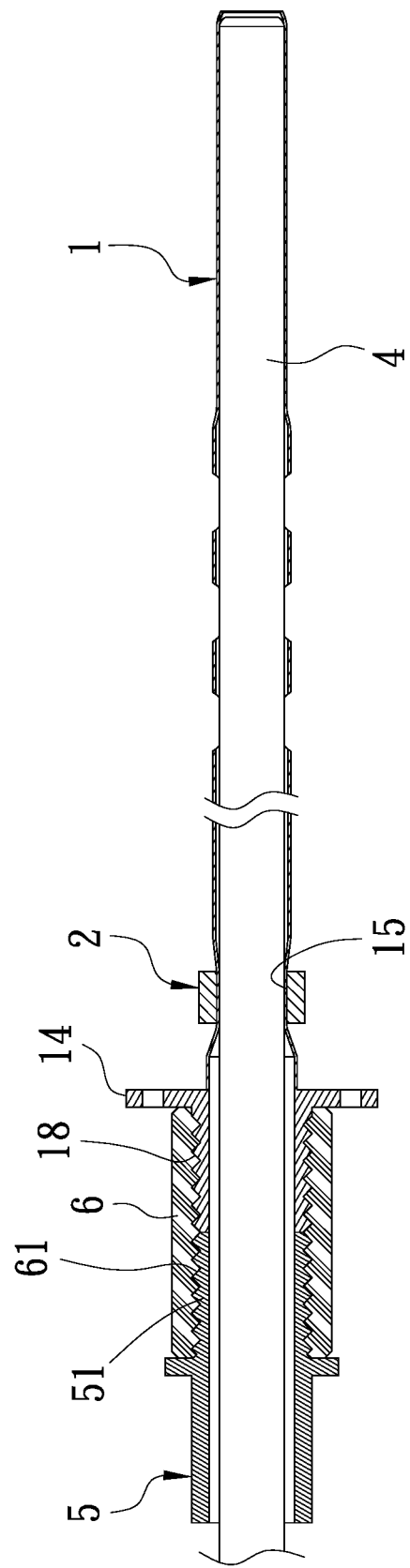
FIG. 3 is a side sectional view showing the nasogastric tube structure sleeved on the transnasal gastroscope in the first embodiment of the present invention in which the positioning member is fixed with the two positioning segments.
Figure 4:
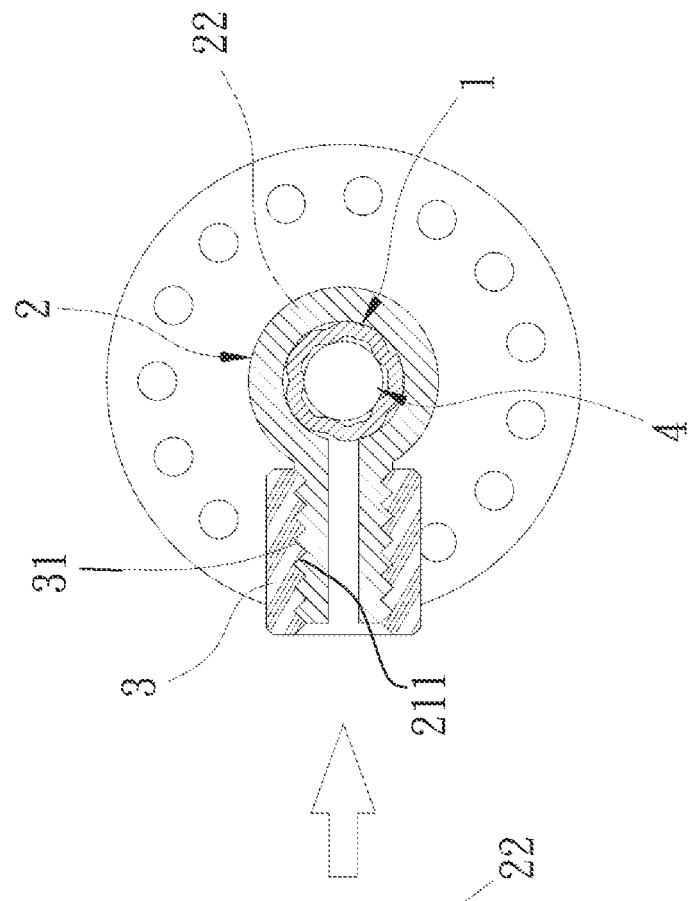
FIG. 4 is a front sectional view showing the positioning member unfixed and fixed with the two positioning segments in the first embodiment of the present invention.
Figure 4:
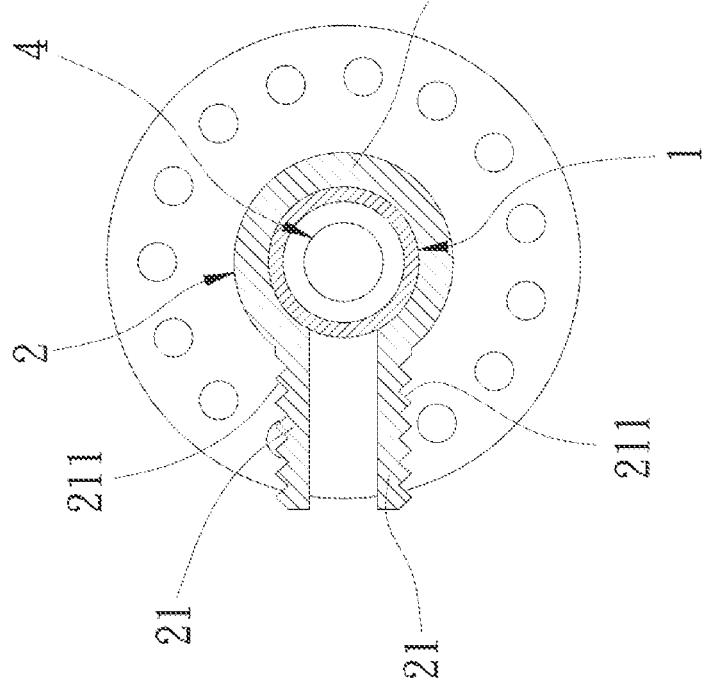

In one embodiment in FIG. 1 to FIG. 3, the diameter of the first tube (1) is similar along an axis from the front necking opening (11) to the rear opening (12).

Figure 14:
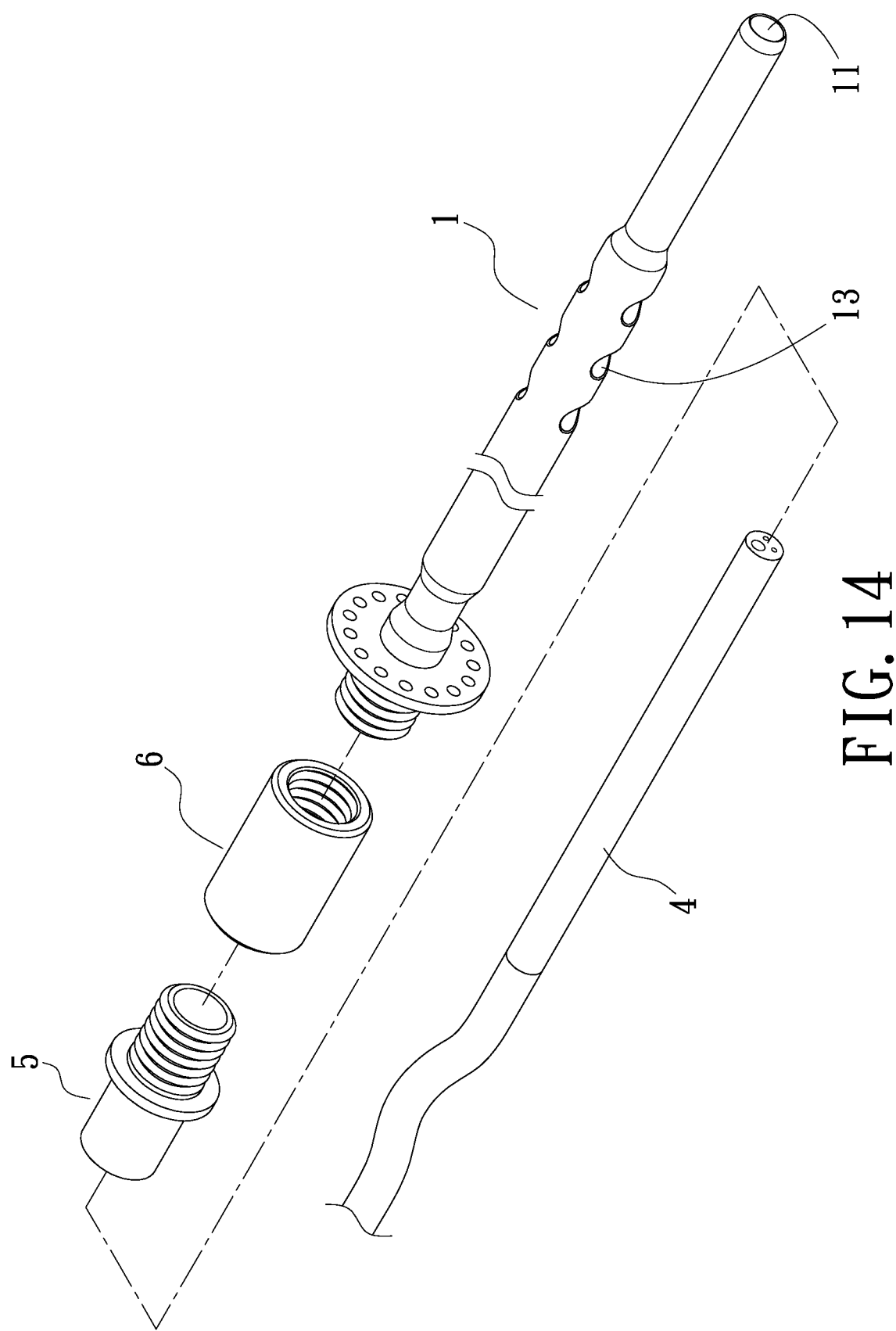
FIG. 14 is an exploded diagram showing a first tube of the present invention having a wider rear segment than a front segment thereof.

In one embodiment in FIG. 14, a rear section of the first tube (1) has a larger diameter than a diameter of a front section of the first tube (1).

Figure 15:
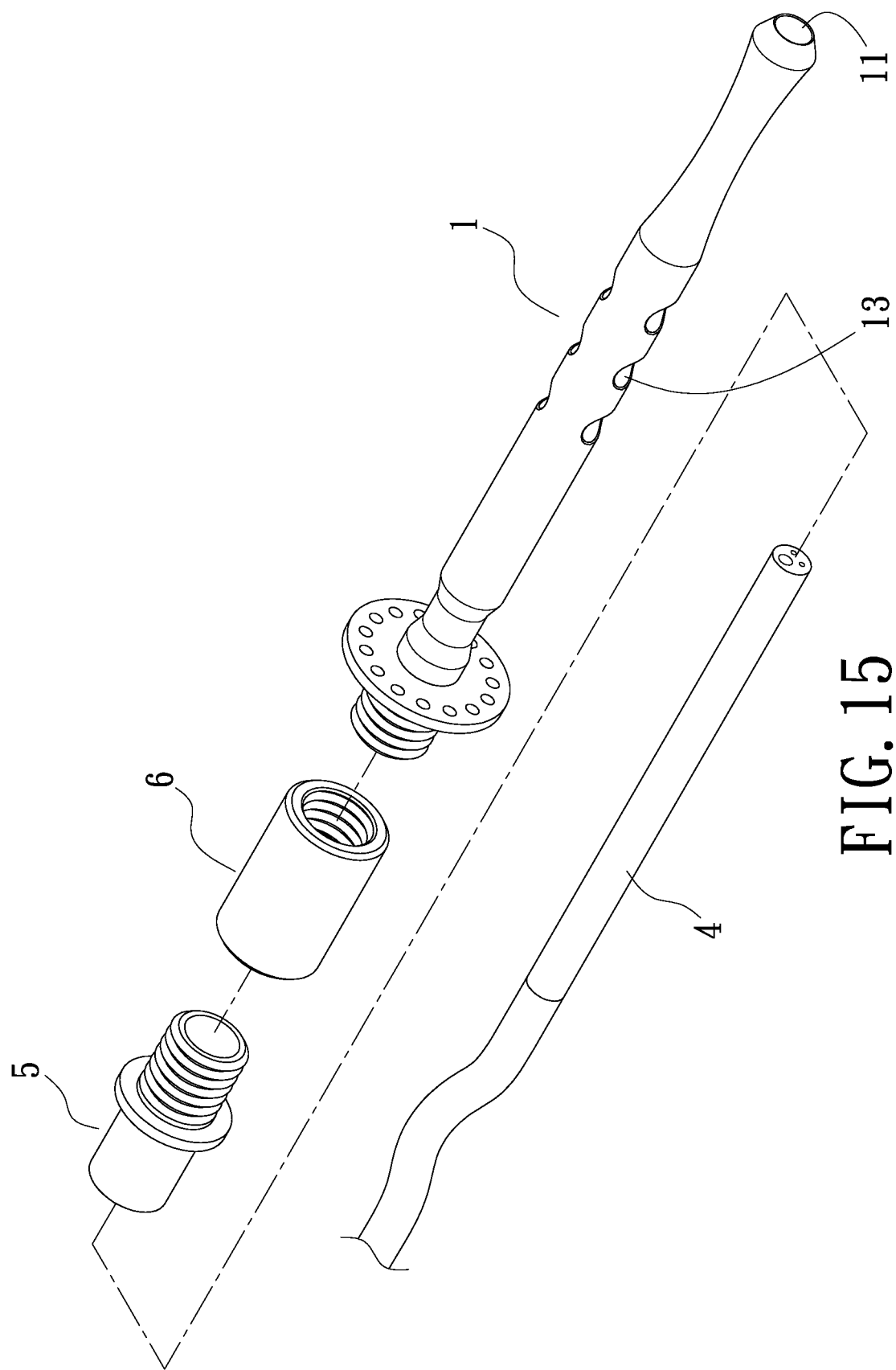
FIG. 15 is an exploded diagram showing a first tube of the present invention having a front segment tapered along an axial direction and then gradually widened to form a curved concaved portion.
Figure 16:
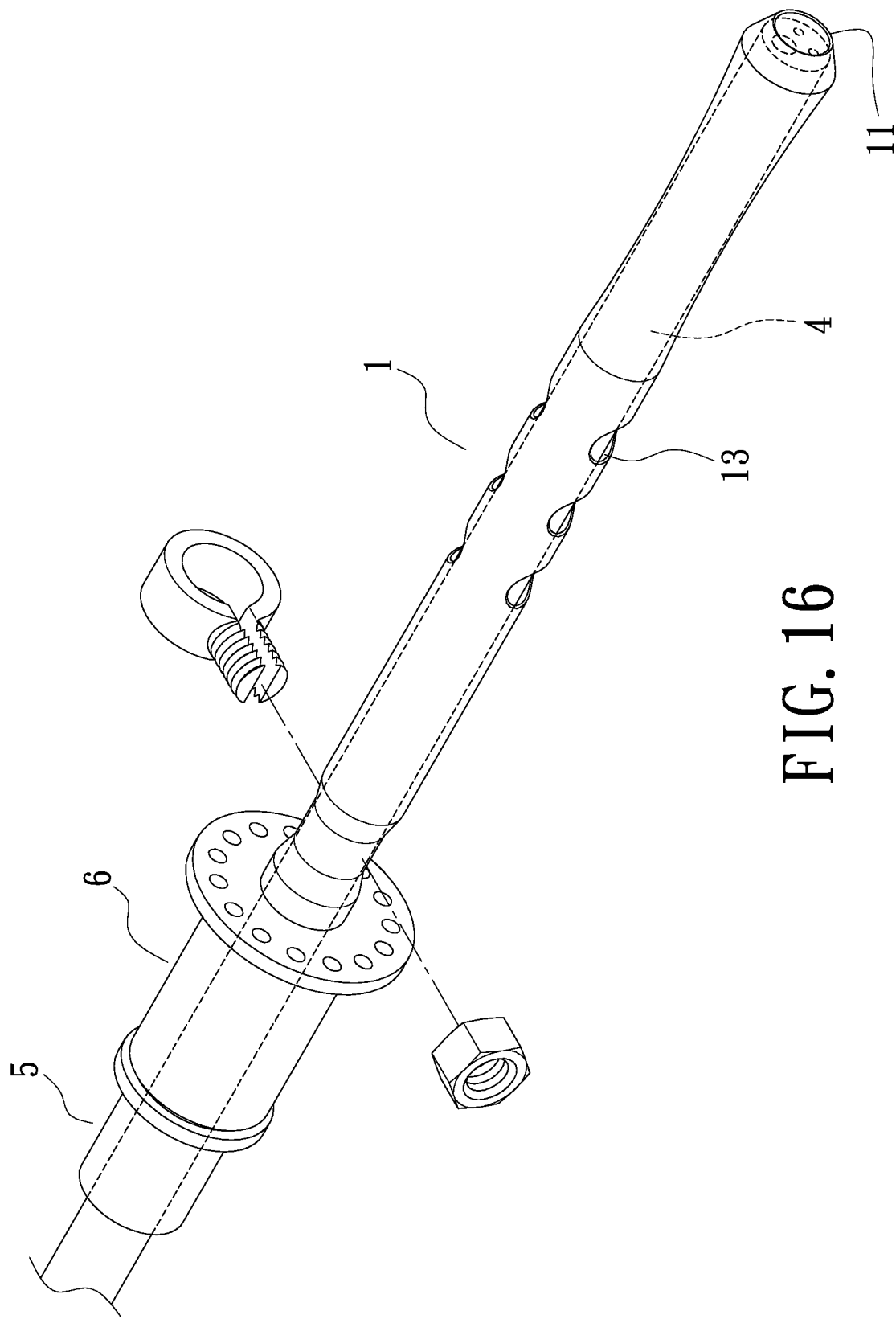
FIG. 16 is a stereogram showing the nasogastric tube structure sleeved on a transnasal gastroscope according to FIG. 15 of the present invention in which a positioning member is unfixed with two positioning segments.
Figure 17:
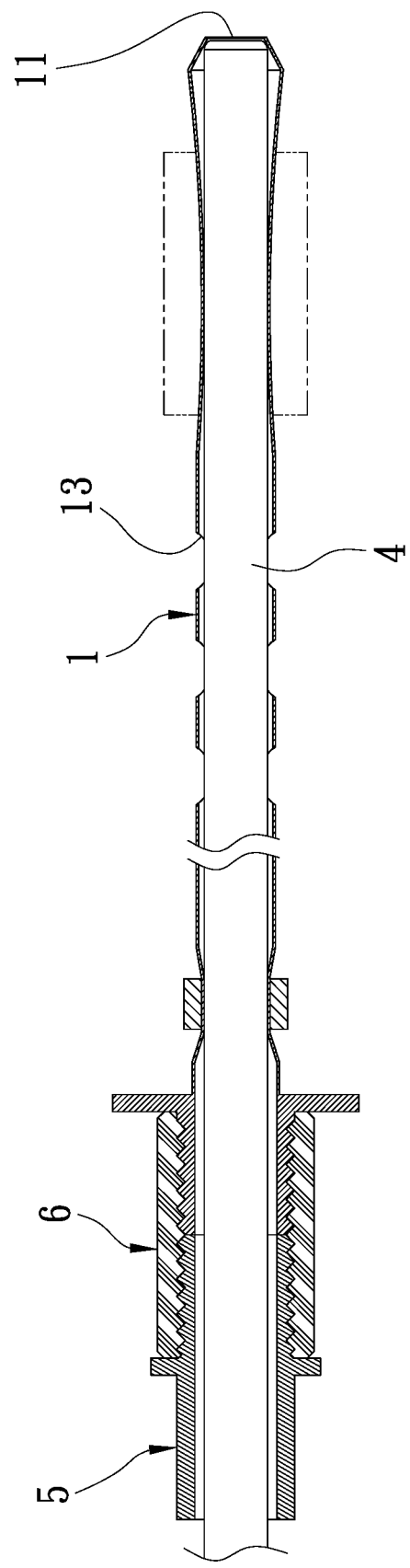
FIG. 17 is a sectional view showing the nasogastric tube structure sleeved on the transnasal gastroscope according to FIG. 15 of the present invention in which a positioning member is fixed with two positioning segments.

In FIG. 15 to FIG. 17, the front segment of the first tube (1) is tapered along an axial direction from the front necking opening (11) thereof and then gradually widened to form a curved concaved portion of the front segment.

Figure 18:
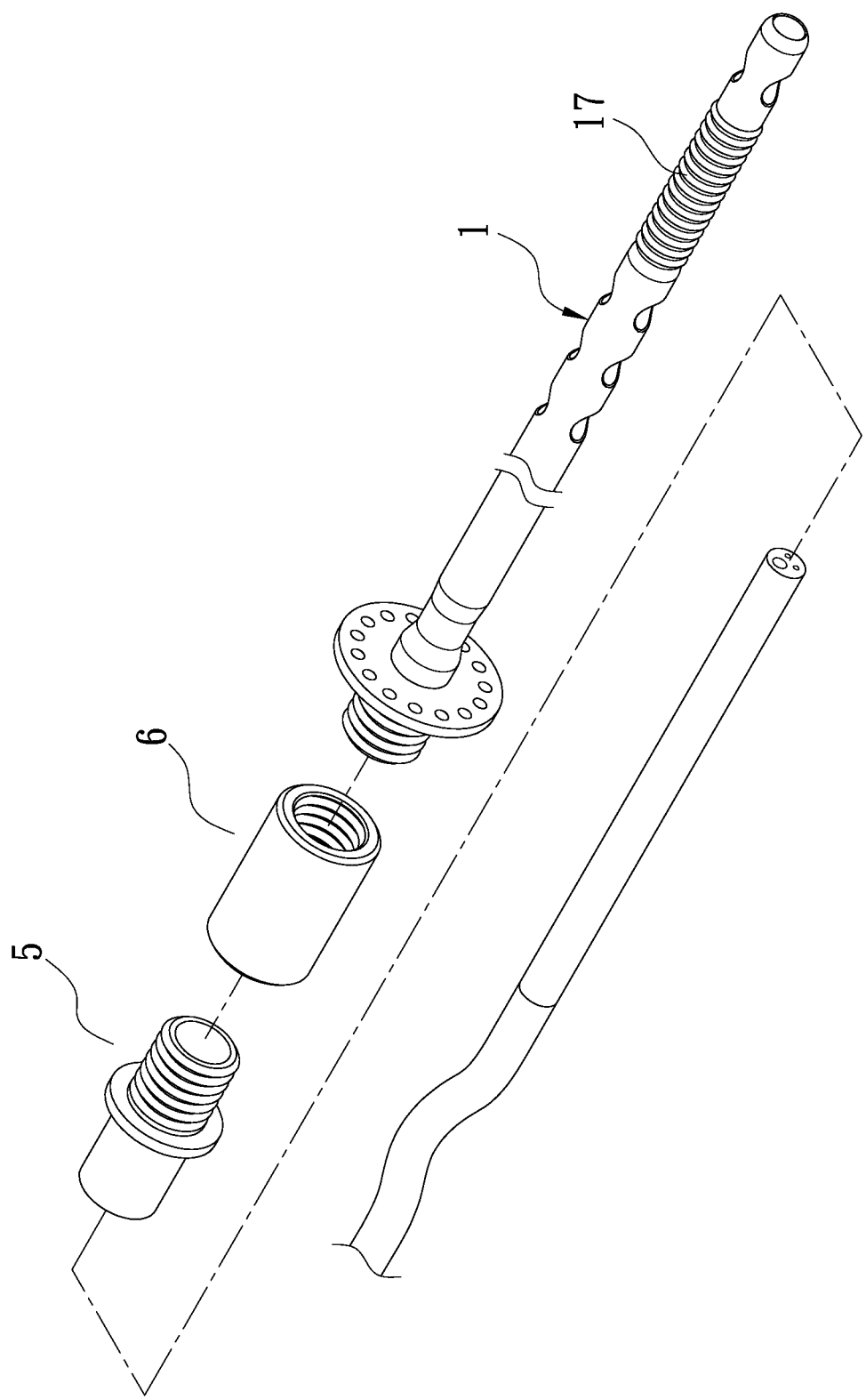
FIG. 18 is an exploded diagram showing a nasogastric tube having a thin first tube and a bendable section at a front segment of the thin first tube of the present invention.

In one embodiment in FIG. 18, the first tube (1) further has a bendable section (17) at the front segment thereof.

Figure 19:
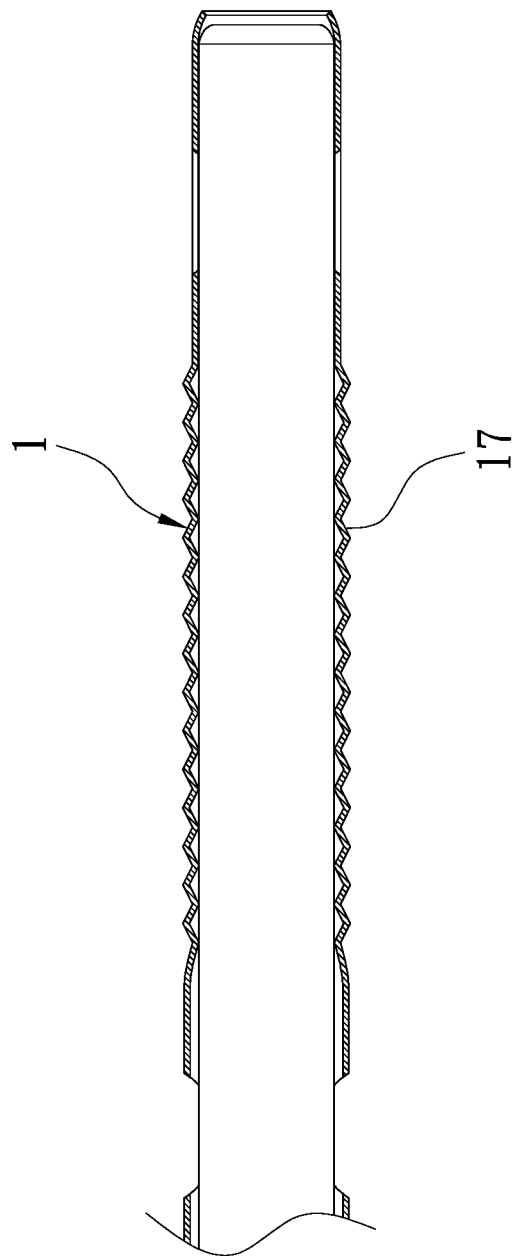
FIG. 19 is a side sectional view showing a bendable section of a first tube as a bellows tube having a jagged section of the present invention.
Figure 20:
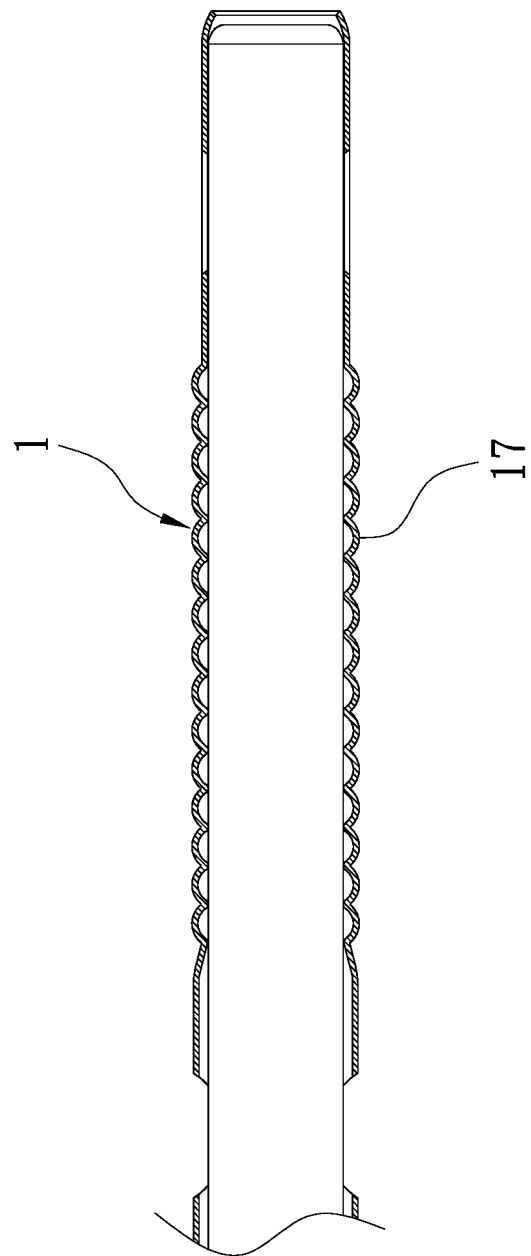
FIG. 20 is a side sectional view showing a bendable section of a first tube as a bellows tube having an arc-shaped section of the present invention.

In FIG. 19, the bendable section (17) is a bellows tube having a jagged section; and in FIG. 20, the bendable section (17) is a bellows tube having an arc-shaped section.

Figure 21:
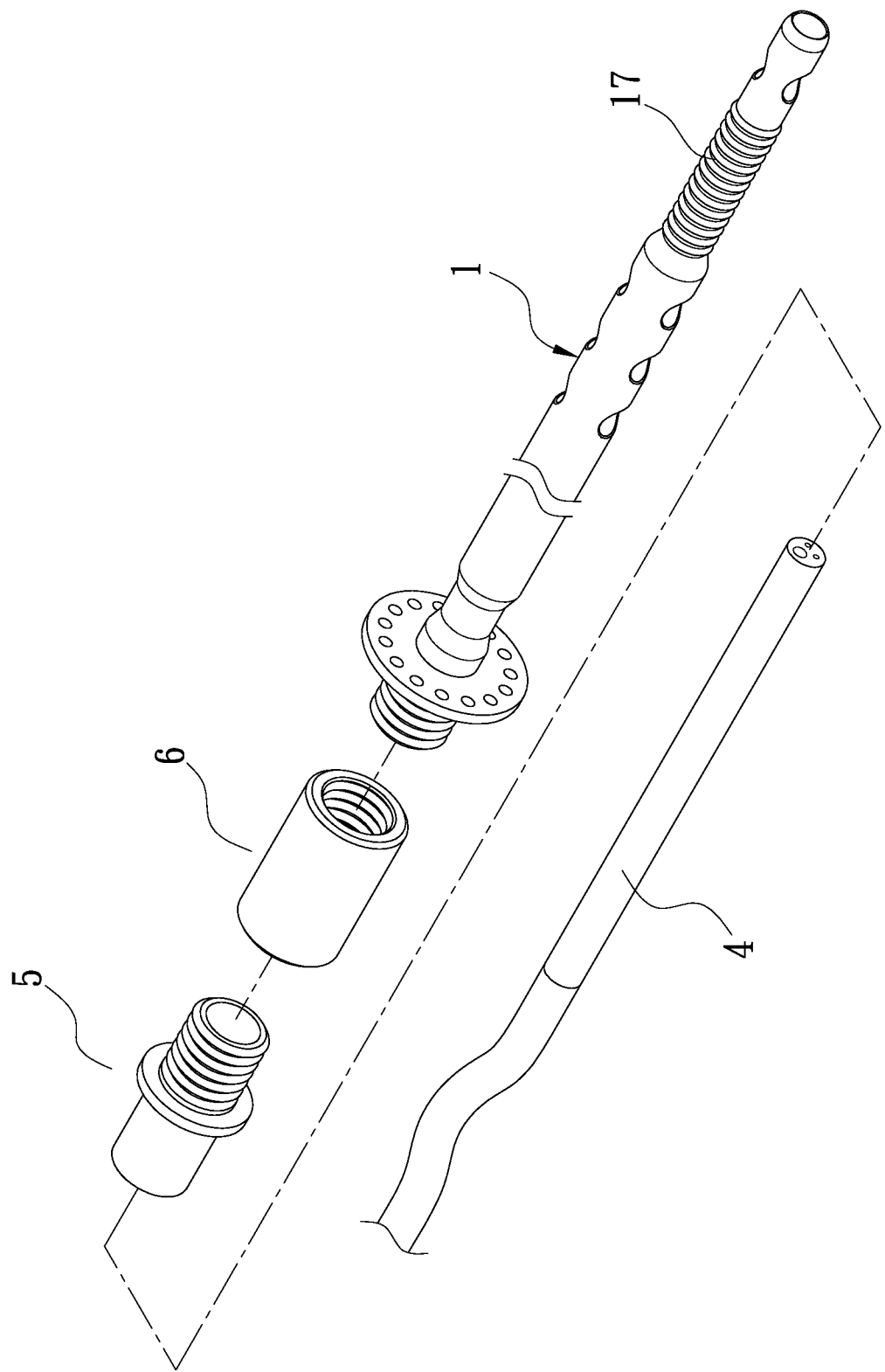
FIG. 21 is an exploded diagram showing a nasogastric tube structure having a thick first tube and a bendable section at a front segment of the thick first tube of the present invention.
Figure 22:
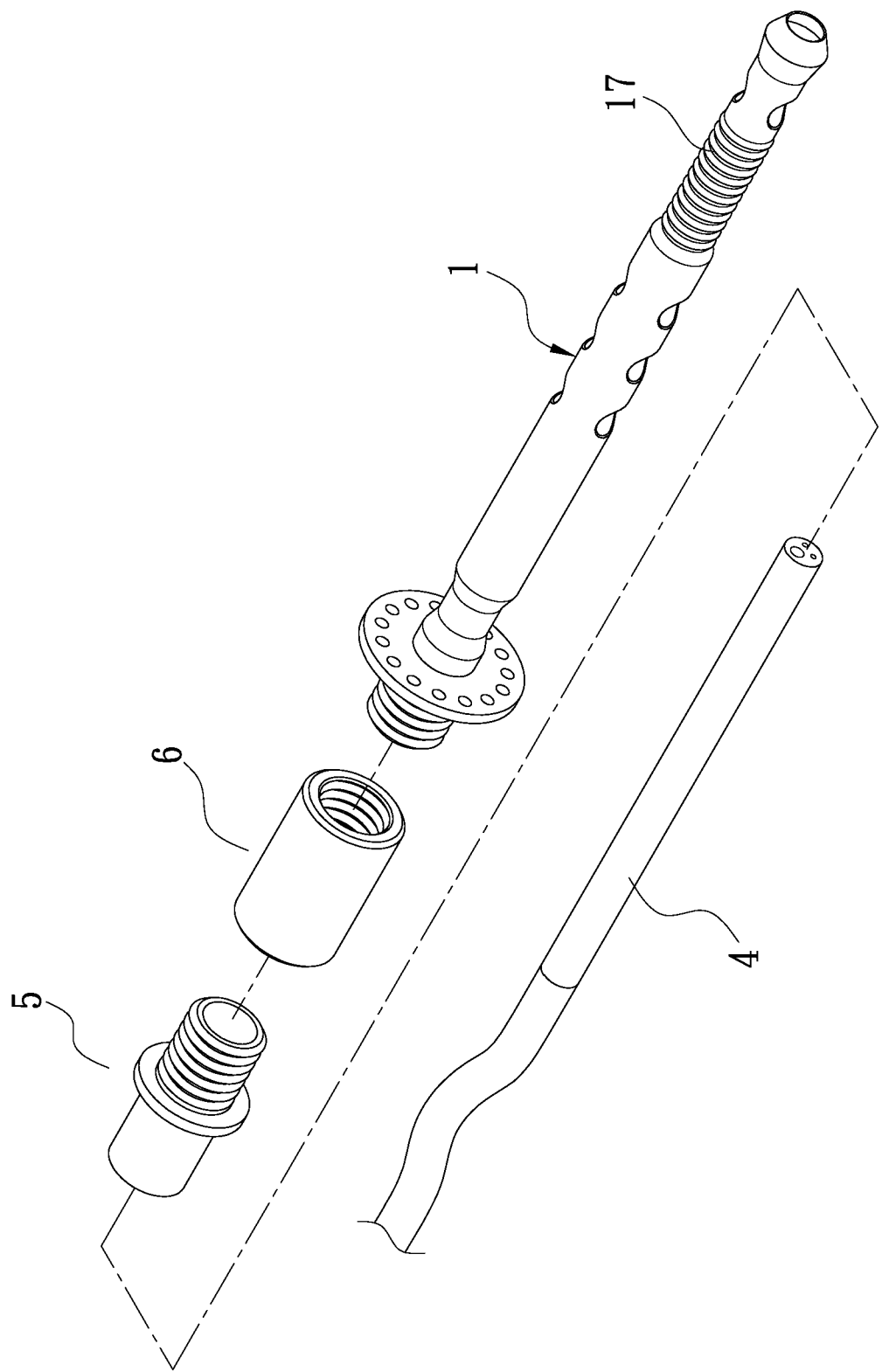
FIG. 22 is an exploded diagram showing a nasogastric tube structure of the present invention used in FIG. 15 to FIG. 17.

In FIG. 18, the bendable section (17) is installed on the first tube (1) shown in FIG. 1 to FIG. 3; in FIG. 21, the bendable section (17) is installed on the first tube (1) shown in FIG. 14; and in FIG. 22, the bendable section (17) is installed on the first tube (1) shown in FIG. 15 to FIG. 17.

In embodiments shown in FIG. 1 to FIG. 22, each of the nasogastric tube structure of the present invention further comprises a second tube (5) and a connector (6). The connecter (6) is shaped as a tubular structure and having a connection portion (61) on an inner wall thereof. The first tube (1) has a first connecting terminal (18) at a back end thereof and the second tube (5) has a second connecting terminal (51) at a front end thereof for respectively engaging with the connection portion (61) of the connector (6).

The user can engage the second tube (5) with the first tube (1) or remove the second tube (5) from the first tube (1) according to the actual situation due to a character of movable assembly or separation between the first tube (1), the second tube (5) and the connector (6). For instance, the second tube (5) is removed during non-tube feeding period to prevent the second tube (5) hanging outside the nose of the user and reduce attention by other people because of a different appearance of the user. The user can put on a sanitary mask after the second tube (5) is removed, so the nasogastric tube structure is not observed by other people to improve confidence of the user.

What is claimed is:

1. A nasogastric tube device, comprising:
    a transnasal gastroscope having a longitudinally extended body with a certain outside diameter and a distal end;
    a first tube configured for insertion through a nasal cavity and esophagus into a patient's stomach and having opposing proximal and distal terminal ends and a lumen extending from a rear opening at the proximal terminal end to a front opening in the distal terminal end, the distal terminal end being necked down to a reduced diameter at the front opening, the first tube having an intermediate portion extending between the proximal and distal terminal ends, at least one through hole penetrating a wall of the intermediate portion being formed adjacent to the necked down distal terminal end, the intermediate portion being formed with an engaging groove defining an annular recess located adjacent to the rear opening, the longitudinally extended body of the transnasal gastroscope being removably sleeved in the lumen of the first tube, the front opening having a diameter less than the certain outside diameter of the longitudinally extended body of the transnasal gastroscope to thereby prevent passage of the distal end of the longitudinally extended body of the transnasal gastroscope therethrough;
    a clamping member engaged with the engaging groove of the first tube with the longitudinally extended body of the transnasal gastroscope being disposed in the lumen of the first tube and having two corresponding positioning segments and a C-shaped clip portion connected to the two positioning segments by two ends thereof; and
    a positioning member sleeved on the two positioning segments simultaneously for holding the two positioning segments closely to compress a wall portion of the first tube corresponding to the annular recess into contact with the longitudinally extended body of the transnasal gastroscope and thereby generate a fixing force by the C-shaped clip portion to releasably lock the first tube to the longitudinally extended body of the transnasal gastroscope.

2. The nasogastric tube device as claimed in claim 1, wherein each of the two positioning segments has an outer screw thread at an outer surface, and the positioning member has an inner screw thread for screwing the outer screw thread of each of the two positioning segments to fix the positioning member.

3. The nasogastric tube device as claimed in claim 2, further comprising a second tube and a connector shaped as a tubular structure and having a connection portion on an inner wall thereof, and wherein the first tube has a first connecting terminal at a back end thereof and the second tube has a second connecting terminal at a front end thereof for respectively engaging with the connection portion of the connector.

4. The nasogastric tube device as claimed in claim 1, wherein the positioning member has a tunnel for sleeving the two positioning segments and fixing the positioning member to the two positioning segments.

5. The nasogastric tube device as claimed in claim 4, wherein the first tube has a stopper ring on a wall thereof adjacent to both the rear opening and the engaging groove, the stopper ring having plural apertures.

6. The nasogastric tube device as claimed in claim 4, further comprising a cap having a photosensitive layer on a surface thereof at the front opening.

7. The nasogastric tube device as claimed in claim 6, wherein the first tube has a front segment having a first diameter and a back segment having a second diameter, wherein the first diameter of the front segment is less than the second diameter of the back segment, or wherein the front segment is tapered along an axial direction thereof and then gradually widened to form a curved concaved portion of the front segment.

8. The nasogastric tube device as claimed in claim 7, wherein the first tube has a bendable section at the front segment thereof.

9. The nasogastric tube device as claimed in claim 8, wherein the bendable section is a bellows tube having a jagged section or an arc-shaped section.

10. The nasogastric tube device as claimed in claim 9, further comprising a second tube and a connector shaped as a tubular structure and having a connection portion on an inner wall thereof, and wherein the first tube has a first connecting terminal at a back end thereof and the second tube has a second connecting terminal at a front end thereof for respectively engaging with the connection portion of the connector.

11. The nasogastric tube device as claimed in claim 4, further comprising a second tube and a connector shaped as a tubular structure and having a connection portion on an inner wall thereof, and wherein the first tube has a first connecting terminal at a back end thereof and the second tube has a second connecting terminal at a front end thereof for respectively engaging with the connection portion of the connector.

12. The nasogastric tube device as claimed in claim 1, further comprising a second tube and a connector shaped as a tubular structure and having a connection portion on an inner wall thereof, and wherein the first tube has a first connecting terminal at a back end thereof and the second tube has a second connecting terminal at a front end thereof for respectively engaging with the connection portion of the connector.

13. The nasogastric tube device as claimed in claim 1, wherein the transnasal gastroscope has a camera disposed at the distal end thereof, the camera being exposed through the front opening of the first tube when the transnasal gastroscope is sleeved in the lumen of the first tube.

\* \* \* \* \*